Figure 1:
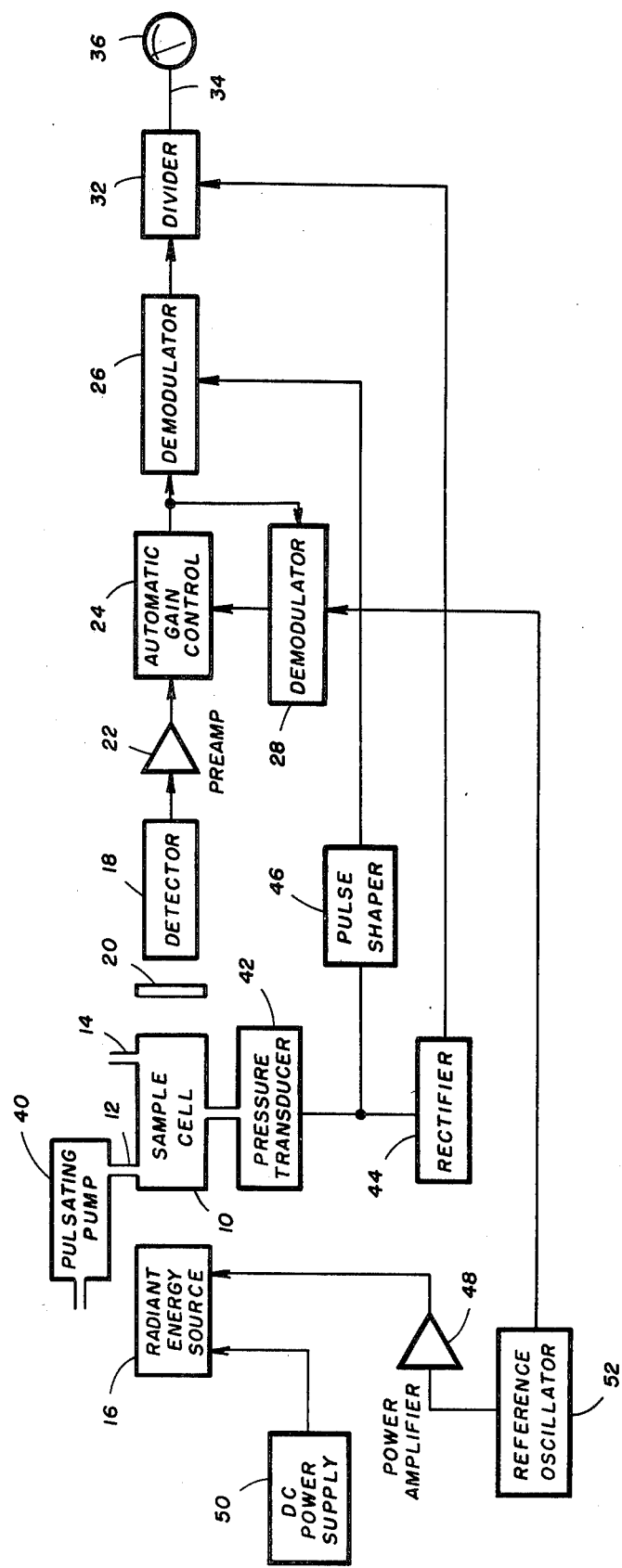

United States Patent [19]

Burough

[11] 4,163,899

[45] Aug. 7, 1979

[54] METHOD AND APPARATUS FOR GAS ANALYSIS

[75] Inventor: Irvin G. Burough, Walnut Creek, Calif.

[73] Assignee: Andros, Inc., Berkeley, Calif.

[21] Appl. No.: 916,609

[22] Filed: Jun. 19, 1978

Related U.S. Application Data

[63] Continuation-in-part of Ser. No. 855,895, Nov. 30, 1977, abandoned.

[51] Int. Cl.² ............................................. G01J 1/00
[52] U.S. Cl. .................................................. 250/343
[58] Field of Search ............... 250/343, 344, 345, 373; 356/51

[56] References Cited

U.S. PATENT DOCUMENTS

| | | | |
|---|---|---|---|
| 2,758,216 | 8/1956 | Luft | 250/345 |
| 3,005,097 | 10/1961 | Hummel | 250/343 |
| 3,679,899 | 7/1972 | Dimeff | 250/343 |
| 4,027,972 | 6/1977 | Davies | 250/343 |

Primary Examiner—Alfred E. Smith
Assistant Examiner—Carolyn E. Fields
Attorney, Agent, or Firm—Fitch, Even & Tabin

[57] ABSTRACT

A method and apparatus are described for detecting a selected gas in an unknown gas sample. The power output of a radiant energy source is modulated at a first frequency and passed through the sample, the density of the sample being varied at a second frequency. The radiant energy passing through the sample is detected by and converted to an electrical signal which is then processed in order to produce an output signal representative of the selected gas. Density of the sample is preferably modulated or varied periodically by means of a pulsating pump which also supplies the unknown gas.

9 Claims, 2 Drawing Figures

METHOD AND APPARATUS FOR GAS ANALYSIS

This is a continuation-in-part of Application Ser. No. 855,895, filed Nov. 30, 1977 and now abandoned.

This invention relates generally to a method and apparatus for analyzing an unknown gas sample to detect the presence and concentration of a selected gas. More specifically, the invention relates to such a method and apparatus where a particularly simple and compact analyzer including only a single gas chamber is employed for detection of the selected gas.

The method and apparatus of the present invention may be used to particular advantage in the measurement of moderate to low concentrations of many pollutant, toxic, or anesthetic gases such as carbon dioxide, methane or nitrous oxide, for example. As noted above, the method and apparatus of the invention permit the use of particularly compact apparatus having the additional desirable advantages of simplicity and minimum power requirements so that the analyzer may be employed in a portable, battery-powered configuration. The manner in which the present invention accomplishes these general objectives is described in greater detail below.

In general, nondispersive gas analysis techniques are well known in the prior art. For example, a method and apparatus employed for determining the presence or absence of a known gas in an unknown gas mixture and the amount of the known gas therein is set forth in U.S. Pat. No. 3,679,899, issued July 25, 1972, to Dimeff. Additional examples in the prior art of such nondispersive gas analysis technique include U.S. Pat. No. 3,005,097, issued Oct. 17, 1961, to Hummel; U.S. Pat. No. 2,758,216, issued Aug. 7, 1956, to Luft; and also U.S. Pat. No. 4,027,972, issued June 7, 1977, to Donald W. Davies and assigned to the assignee of the present invention.

The methods and apparatus described or suggested by these prior art references generally require relatively complex, bulky, and expensive equipment. For example, it may be seen that such prior art techniques typically require a plurality of gas chambers for containing an unknown sample and one or more standard gases and which are arranged along the path of a radiant energy beam. In addition, the prior art means for varying pressure within the sample cell typically utilizes yet another chamber in communication with the sample cell or else relatively complex driver means within the sample cell itself.

Accordingly, there remains a need for a method and apparatus for detecting the presence and concentration of a selected gas in an unknown gas sample which may be carried out in a simple and reliable manner by means of compact, low cost gas analysis equipment.

Accordingly, it is an object of the invention to provide an improved method and apparatus for detecting the presence and measuring the concentration of a selected gas within an unknown gas sample.

Another object of the invention is to provide a simple, low cost, and reliable method and apparatus for detecting the presence and measuring the concentration of a selected gas within an unknown gas sample.

Figure 2:
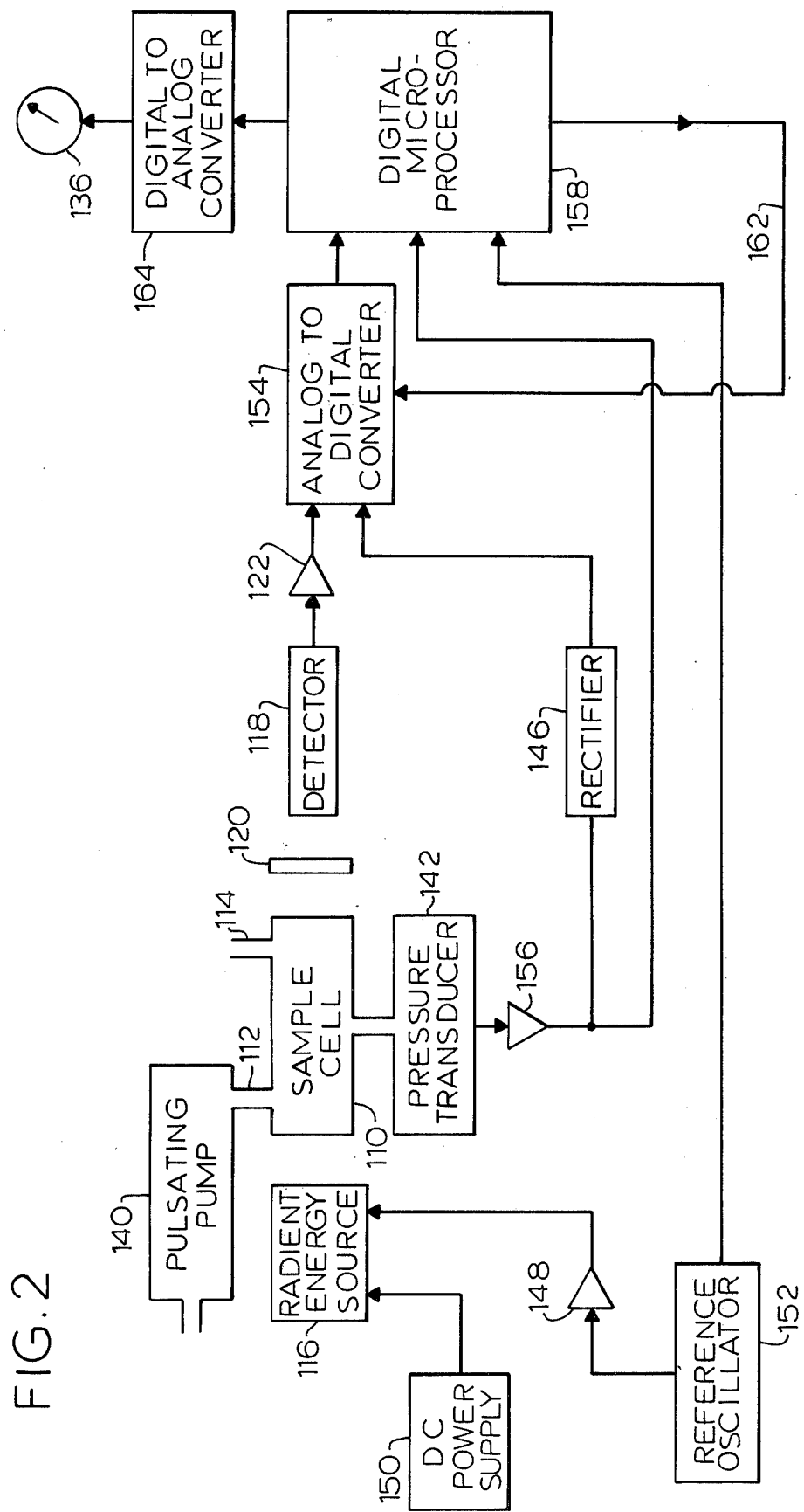

Other objects of the invention will become apparent from the accompanying drawings wherein:

FIG. 1 is a schematic block diagram of a preferred form of the apparatus of the invention; and FIG. 2 is a schematic block diagram of another embodiment of the invention.

More specifically, the method and apparatus of the present invention contemplate use of a radiant energy source 16 having a wave length spectrum including characteristic absorption wave lengths of a selected gas. The power output of the source is modulated at a first frequency and passed through a sample volume or cell 10 of the unknown gas. Absorption of radiant energy within the sample volume is modulated by varying the density of the gas therein at a second frequency. Radiant energy at the characteristic wave length passing through the sample volume is then detected in a detector 18 and processed to provide the desired information.

Referring now in more detail to the drawings, the method and apparatus of the invention may be best understood by a description of the construction and operation of the illustrated apparatus of FIG. 1 and its mode of operation. A gas analysis device is schematically represented within the drawing and includes the sample cell 10 wherein an unknown gas mixture may be introduced through an inlet port 12 and may exit through a suitable outlet port 14. The manner in which the unknown gas is supplied to the sample cell is described in greater detail below.

The radiant energy source 16 is arranged to direct a beam of radiant energy through the sample cell 10 for impinging on the detector 18. The radiant energy source 16 is selected to have a wave length spectrum sufficiently broad to encompass the characteristic absorption wave length or wave lengths for the selected gas to be detected. Preferably, the radiant energy source 16 is an infrared source which emits infrared energy, at least when the gas analysis method and apparatus of the invention are employed for the detecting of gases such as carbon dioxide having a wave length included within the infrared spectrum.

As noted above, the detector 18 receives or detects radiant energy from the source 16 which is not absorbed within the sample cell 10. The radiant energy received by the infrared detector 18 also passes through a narrow band interference filter 20 which is preferably arranged between the sample cell 10 and the detector 18. The interference filter 20 is selected to pass that portion of radiation or radiant energy which includes a characteristic absorption wave length band of the selected gas.

The specific construction of the sample cell 10, the interference filter 20 and the detector 18 may be of generally conventional construction as is well described within the prior art in order to permit radiant energy from the source 16 to pass through the gas within the sample cell and through the interference filter 20 to impinge upon the detector 18. However, the manner in which the gas is supplied to the sample cell 10 and the manner in which radiant energy from the source 16 is modulated are described in detail below since they comprise particularly important features of the present invention.

Initially, the unknown gas sample is supplied into the sample cell 10 through the inlet 12 by means of the pulsating pump 40 which may be of a diaphragm, piston or bellows type construction and operation. The specific sizing and capacity of the pump are determined with respect to the volume of the sample cell 10 and the size of the gas outlet 14. The pump 40 is specifically selected to be of a pulsating type in order to produce nearly uniform cyclical density variation or pressure excursion within the sample cell 10.

Pressure variations, proportional to the density excursions within the sample cell 10, are detected by a suitable pressure transducer 42. The pressure transducer thereby produces a reference signal having a frequency of that of the density excursions within the sample cell 10. This signal is processed as described below.

Modulation of the radiant energy in the source 16 may be accomplished by means of the reference oscillator 52 which is coupled to the source 16 through a suitable power amplifier 48. In addition, the source is powered from a DC power supply (battery) 50 on which the AC power from the amplifier 48 is superimposed. A square wave output of the reference oscillator 52 is also applied to the demodulator 28 as a signal of the oscillator frequency for phase information. As an alternative, the frequency of the source modulation may be derived directly from the power utility line, thus eliminating the need for the reference oscillator 52. Timing information may also be obtained from any other suitable available source, such as a microprocessor.

The detector 18 may be of a lead selenide type, for example. The output signal from the detector 18 is a composite of signals at the first and second frequencies and is processed along with the reference signal to provide the desired information.

More particularly, the electrical signal from the detector 18, at the second frequency, is proportional to:

(a) The radiant energy passing through the sample cell 10.

(b) The amplitude of modulation of the sample gas.

(c) The concentration of the selected gas within the unknown sample.

The signal at the first frequency is proportional to (a), the radiant energy. A signal proportional to (b), the amplitude of gas modulation, is obtained from a pressure transducer 42 located in the sample cell. This signal is also at the second frequency.

To produce a resultant output signal which is proportional only to the concentration of the selected gas within the unknown gas sample, the signals are suitably processed by analog or digital means. The output signal derived from this processing is proportional to the amplitude of the signal component at the second frequency divided by the product of the amplitude of the signal component at the first frequency and the reference signal. This signal is proportional to the unknown gas concentration in the sample cell 10, is independent of the radiant flux intensity, and is also independent of the amplitude of the pressure excursion in the sample cell.

One way of suitably processing the signals by analog techniques is to apply the composite detector output through a preamplifier 22 to an automatic gain control (AGC) means or device 24. One type of AGC device which is satisfactory for this purpose is Model No. MC-3340-P available from Motorola, Inc., Phoenix, Ariz. The output of the AGC is connected to a first demodulator 28 and a second demodulator 26. On the first demodulator 28, the signal (originating from the detector) at the first frequency is phase and frequency lock rectified to a DC value, using the square wave output of the reference oscillator as the reference input to the demodulator. The DC output of the demodulator is compared to a fixed DC voltage, and the difference between these two voltages is servo controlled to null by using the demodulator output to control the AGC gain. In this manner the output of the AGC contains the signal at the first frequency servo controlled to a constant amplitude. The same gain adjustment is made by the AGC to the signal at the second frequency whose value is then independent of the radiant energy source output.

The output signal from the AGC is also passed to a second demodulator 26, wherein the signal at the second frequency is phase and frequency lock rectified to a DC value, using the square wave output from the pulse shaper 46 as the reference input to the demodulator. Both of the demodulators 26 and 28 may be of identical construction and may, for example, be synchronous rectifiers such as Model 129 available from Princeton Applied Research, Princeton, N.J. The same function may be obtained at lower cost using conventional solid state components. The resulting DC signal is then independent of the signal component at the first frequency.

The output of the demodulator 26 is now applied as the numerator to the divider circuit 32. The divider 32 may, for example, be Model AD532 available from Analog Devices Inc., Santa Clara, Calif. The denominator input of the divider circuit is the output from a rectifier 44.

The output of the transducer 42 is coupled to a pulse shaper 46 and to the rectifier 44. The pulse shaper 46 may be a conventional amplitude limiting amplifier and provides a square wave output at the pump (second) frequency to the demodulator 26. The rectifier 44 provides a DC signal, proportional to the pressure amplitude within the sample cell, to the divider 32. The divider output 34 is thus a signal proportional only to the unknown gas concentration. The divider output 34 may be displayed on any suitable readout means 36, such as an analog meter or digital display by way of example, as a means of indicating the concentration of the gas of interest within the unknown sample supplied to the sample cell 10 by the pump 40.

Referring now to FIG. 2, a further embodiment of the invention is illustrated wherein the requisite signal processing is carried out digitally. The processing of the energy from the radiant energy source and the development of the requisite signals is accomplished in this embodiment by means similar to that shown in FIG. 1, and elements of FIG. 2 having a function substantially identical to elements of FIG. 1 have been given the same reference numerals preceded by a 1.

The detector output developed in the preamplifier 122 of FIG. 2 is applied to an analog to digital converter 154. The analog signal from the pressure transducer developed by the rectifier 146 coupled to the output of the pressure transducer amplifier 156 is also applied to the analog to digital converter 154. Thus, analog information representing the composite signal in the detector 118, and also representing the magnitude of the pressure excursion in the sample cell, is developed into corresponding digital information. This digital information is applied from the analog to digital converter to a suitable digital microprocessor 158.

Also providing digital information to the microprocessor 158 is the pressure transducer amplifier 156, which provides frequency information to the microprocessor. Frequency information is also provided to the microprocessor from the reference oscillator 152. For the purpose of multiplexing the analog to digital converter 154 as is known in the art, as well as for the purpose of initiating the conversion itself, a feedback connection 162 is provided between the output of the microprocessor and the converter 154.

The digital microprocessor 158 may be of any suitable design to process the digital information supplied to it to derive the same information previously described in connection with the analog circuitry of FIG. 1. The digital information corresponding to the detector signal will be proportional to the radiant energy passing through the sample cell 110, the amplitude of modulation of the sample gas, and the concentration of the selected gas within the unknown sample. The resultant output signal, which is proportional only to the concentration of the selected gas within the unknown gas sample, is derived from dividing the detector signal component at the second frequency by the product of the amplitude of the detector signal component at the first frequency and the reference signal from the reference oscillator 152. The particular algorithm for accomplishing this in the microprocessor may be of any suitable design consistent with the available microprocessor capability. In some cases, it may be necessary to provide a frequency doubler for doubling the pressure transducer frequency signal applied to the microprocessor.

The output of the digital microprocessor 158, which is a signal proportional to the unknown gas concentration in the sample cell 110, and which is independent of the radiant flux intensity and the amplitude of the pressure excursion in the sample cell, may be processed in any suitable way. For example, such signal may be applied to a suitable computer for further processing. In FIG. 2, this signal is shown being applied to a digital to analog converter 164 which converts the digitally processed output back into an analog signal for application to a suitable indicator or meter 136.

Although shown and described in connection with a microprocessor, it will be apparent to those skilled in the art that the necessary signal processing may be accomplished by other suitable means as well as the specific analog and digital means described and illustrated. For example, if the gas analyzer of the invention is to be utilized in connection with other equipment which already contains digital processing means, such means may be utilized on a partial or time-shared basis to accomplish the desired signal processing for the gas analyzer.

Various modifications of the invention in addition to those described above and shown within the accompanying drawings will be apparent to those skilled in the art and any such modifications are intended to fall within the scope of the present invention which is defined only by the appended claims.

What is claimed is:

1. A method for detecting the concentration of a selected gas in an unknown gas sample, comprising, directing from a radiant energy source radiant energy having a wave length spectrum including a characteristic absorption wave length of the selected gas through a sample volume of the unknown gas, modulating the power output of the radiant energy source at a first frequency, simultaneously modulating absorption of the radiant energy within the sample volume by varying gas density therein at a second frequency, detecting the radiant energy passing through the sample volume and producing a composite signal corresponding to said detected radiant energy having first and second components at said first and second frequencies, respectively, producing a reference signal proportional to the amplitude of gas density variation at said second frequency, and processing said composite signal and said reference signal to produce an output signal proportional to the amplitude of the second signal component divided by the product of the amplitude of the first signal and the reference signal, said output signal being proportional to the concentration of the selected gas in the sample.

2. The method of claim 1 wherein the power output of the radiant energy source is modulated at the power line frequency.

3. The method of claim 1 wherein the power output of the radiant energy source is modulated at a fixed fraction thereof.

4. The method of claim 1 wherein the selected gas is carbon dioxide.

5. Apparatus for detecting the concentration of a selected gas in an unknown gas sample, comprising, means for containing a sample volume of the unknown gas, a source for producing radiant energy having a wave length spectrum including a characteristic absorption wave length of the selected gas, means for directing said energy through the sample volume of the unknown gas, first modulating means for modulating the power output of the radiant energy source at a first frequency, second modulating means for simultaneously modulating absorption of the radiant energy within the sample volume by varying gas density therein at a second frequency, means for detecting the radiant energy passing through the sample volume and producing a composite signal corresponding to the detected radiant energy having first and second components at the first and second frequencies, respectively, means for producing a reference signal proportional to the amplitude of gas density variation at the second frequency, and means for processing the composite signal and the reference signal to produce an output signal proportional to the amplitude of the second signal component divided by the product of the amplitudes of the first signal component and the reference signal, said output signal being proportional to the concentration of the selected gas in the sample.

6. The apparatus of claim 5 wherein said first modulating means comprise a reference oscillator for modulating the output of said radiant energy source at the first frequency.

7. The apparatus of claim 5 wherein said second modulating means comprise a pulsating pump means for introducing the unknown gas sample into said sample cell and at the same time causing variation of gas density therein at said second frequency.

8. The apparatus of claim 7 wherein said composite signal adjusting means comprise automatic gain control means.

9. The apparatus of claim 7 wherein said reference signal producing means include pressure transducer means for producing an AC signal at the second frequency and having an amplitude proportional to the pressure excursions in the sample volume.

* * * * *